United States Patent
Dockner et al.

(10) Patent No.: US 9,868,694 B2
(45) Date of Patent: Jan. 16, 2018

(54) PROCESS FOR PREPARING CHLORINATED BIPHENYLANILIDES AND BIPHENYLANILINES

(71) Applicant: BAYER CROPSCIENNCE AKTIENGESELLSCHAFT, Monheim am Rhein (DE)

(72) Inventors: Michael Dockner, Cologne (DE); Lars Rodefeld, Leverkusen (DE); Jens Dietmar Heinrich, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/906,809

(22) PCT Filed: Jul. 18, 2014

(86) PCT No.: PCT/EP2014/065463
§ 371 (c)(1),
(2) Date: Mar. 24, 2016

(87) PCT Pub. No.: WO2015/011032
PCT Pub. Date: Jan. 29, 2015

(65) Prior Publication Data
US 2016/0280635 A1    Sep. 29, 2016

(30) Foreign Application Priority Data

Jul. 23, 2013 (EP) .................................. 13177583

(51) Int. Cl.
| | | |
|---|---|---|
| C07C 231/12 | (2006.01) | |
| C07F 9/50 | (2006.01) | |
| C07F 9/54 | (2006.01) | |
| C07C 209/68 | (2006.01) | |
| C07B 37/04 | (2006.01) | |
| C07C 233/66 | (2006.01) | |

(52) U.S. Cl.
CPC ............ *C07C 231/12* (2013.01); *C07B 37/04* (2013.01); *C07C 209/68* (2013.01); *C07C 233/66* (2013.01); *C07F 9/5004* (2013.01); *C07F 9/5022* (2013.01); *C07F 9/5407* (2013.01); *C07F 9/5442* (2013.01)

(58) Field of Classification Search
CPC ... C07C 231/12; C07C 233/66; C07C 209/68; C07B 37/04; C07F 9/5442; C07F 9/5407; C07F 9/5004; C07F 9/5022
See application file for complete search history.

(56) References Cited

U.S. PATENT DOCUMENTS

| | | | |
|---|---|---|---|
| 6,307,087 B1 | 10/2001 | Buchwald et al. | |
| 6,352,990 B1 | 3/2002 | McCarthy | |
| 8,455,689 B2 | 6/2013 | Dockner et al. | |
| 9,079,875 B2* | 7/2015 | Goossen | B01J 31/1815 |
| 2004/0092762 A1* | 5/2004 | Marhold | C07C 209/68 |
| | | | 560/19 |
| 2010/0185015 A1 | 7/2010 | Straub et al. | |
| 2011/0237799 A1 | 9/2011 | Masaoka et al. | |

FOREIGN PATENT DOCUMENTS

| | | |
|---|---|---|
| EP | 0 888 261 A1 | 1/1999 |
| EP | 2008991 A1 | 12/2008 |
| WO | 2001/042197 A1 | 6/2001 |
| WO | 0142197 A1 | 6/2001 |
| WO | 2004/052939 A2 | 6/2004 |
| WO | 2004052939 A2 | 6/2004 |
| WO | 2006/092429 A1 | 9/2006 |
| WO | 2006092429 A1 | 9/2006 |
| WO | 2007/138089 A1 | 12/2007 |
| WO | 2007138089 A1 | 12/2007 |
| WO | 2009135598 A1 | 11/2009 |

OTHER PUBLICATIONS

International Search Report from corresponding PCT/EP2014/065463, mailed Oct. 22, 2014.
Wolfe et al., "Highly active palladium catalyst for Suzuki coupling reactions", Journal of the American Chemical Society, ACS Publications, (Oct. 1999) vol. 121, No. 41:9550-9561.
Washburn et al. "Annulene", Organic Syntheses Collective, vol. 6, pp. 68-75. 1974.
Dennis G. Hall "Structure, Properties, and Preparation of Boronic Acid Derivatives. Overview of Their Reactions and Applications", Boronic Acids (2005) pp. 1-99.
Kramer et al. "XVII. Reaction of Organometallics With Dialkylborane Derivatives: The Synthesis of Mixed Organoboranes Not Available Via Hydroboration", Journal of Organometallic Chemistry, vol. 73 (1974) pp. 1-15.
Lucas et al. "Some Hypotensive Amino Steroid Glycosides", J. Am. Chem. Soc. (1960) Vol. 82 pp. 5688-5693.

(Continued)

*Primary Examiner* — Jafar Parsa
*Assistant Examiner* — Amy C Bonaparte
(74) *Attorney, Agent, or Firm* — McBee Moore Woodward & Vanik IP, LLC

(57) ABSTRACT

The present invention relates to a process for preparing substituted biphenylanilides of the formula (I).

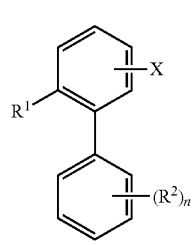

19 Claims, No Drawings

(56) References Cited

OTHER PUBLICATIONS

Fleet "Preparation of Some N-Aminotriazolo-Pyridines and -Quinolines, Their Oxidation With Lead Tetra-Acetate, and the Trapping of the Resulting Pyridynes and Quinolynes With Tetraphenylcyclopentadienone (Tetracyclone)", J. Chem. LSOC (1969) pp. 1758-1763.
Netherton et al. "Air-Stable Trialkylphosphonium Salts: Simple, Practical, and Versatile Replacements for Air-Sensitive Trialkylphosphines. Applications in Stoichiometric and Catalytic Processes", Organic Letters (2001) vol. 3, No. 26, 4295-4298.
Anulewicz-Ostrowska et al "Synthesis of some halogenated tetraarylborates", Tetrahedron Letters No. 44 (2003) 7329-7331.

* cited by examiner

PROCESS FOR PREPARING CHLORINATED BIPHENYLANILIDES AND BIPHENYLANILINES

CROSS REFERENCE TO RELATED APPLICATIONS

This application is a §371 National Stage Application of PCT/EP2014/065463, filed 18 Jul. 2014 which claims priority to EP 13177583.5, filed 23 Jul. 2013.

BACKGROUND

Field of the Invention

The invention relates to an improved process for preparing halogenated biphenylanilides and biphenylanilines by Suzuki coupling of bromo- or iodoanilides or bromo- or iodoanilines with chlorinated organoboron compounds. Biphenylanilides and biphenylanilines serve as precursors for preparation of crop protection agents having fungicidal action.

Description of Related Art

Palladium-catalysed cross-coupling of halogenated aromatics of the formula (II) with organoboron compounds of the formula (III), according to WO 2006/092429, WO 2007/138089 and WO 2009/135598, affords both halogenated biphenylanilines and halogenated biphenylanilides of the general formula (I) according to Scheme 1 below.

Scheme 1

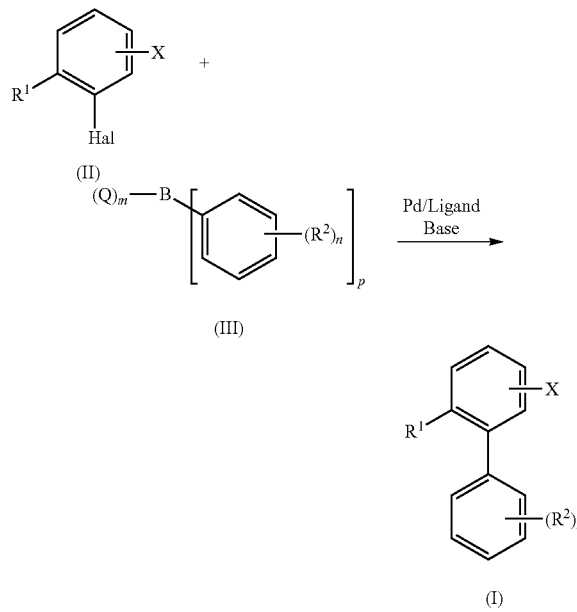

where the substituents are each defined as follows:
X is hydrogen, fluorine or chlorine;
Hal is halogen
$R^1$ is selected from a protected amino group, $NO_2$, $NH_2$ and $NHR^3$;
$R^2$ is selected from cyano, nitro, halogen, $C_1$-$C_6$-alkyl, $C_1$-$C_6$-alkenyl, $C_1$-$C_6$-alkynyl, $C_1$-$C_6$-alkoxy, $C_1$-$C_6$-haloalkyl, ($C_1$-$C_6$-alkyl)carbonyl and phenyl;
$R^3$ is selected from hydrogen, —$CH_2$-(C=O)$CH_3$, $C_1$-$C_8$-alkyl, $C_1$-$C_8$-alkenyl, $C_1$-$C_8$-alkynyl and $C_6$-$C_{18}$-aryl
n is selected from 1, 2 and 3,
p is selected from 1, 2, 3 and 4 and
Q is selected from hydroxyl, F, Cl, Br, I, $C_{1-4}$-alkyl, $C_{6-10}$-aryl, $C_{1-4}$-alkoxy and $C_{6-10}$-aryloxy, $C_{1-4}$-alkoxy radicals which, together with the boron atom to which they are bonded, form a 5- or 6-membered ring which may be substituted by $C_{1-4}$-alkyl radicals
and the compounds of the formula (III) comprise different organoboron compounds.

The ligands used for the Suzuki reaction shown in the above scheme include unsubstituted and substituted trialkyl- or triarylphosphines. In addition, according to WO 2001/042197, dialkylarylphosphines are also suitable as ligands. The selection of possible phosphine ligands is extended by WO 2004/052939, p. 34 ff., to include phosphines in which one of the radicals on the phosphorus consists of a biphenylic base skeleton.

If, in the general formula (II), the substituent
Hal is bromine or iodine, and
X is hydrogen, fluorine or chlorine,

and the substituent $R^2$ in the general formula (III) is chlorine,

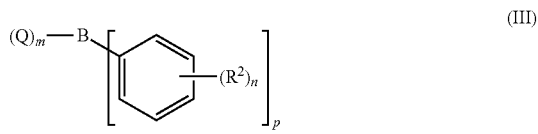

chlorinated biphenylanilide or biphenylaniline formed under the conditions of the Suzuki reaction reacts further with boron compounds of the general formula (III) to give triaryls of the general formula (IV) and higher homologues thereof (Scheme 2). This results in a yield loss of the desired biphenylanilide or biphenylaniline of the general formula (I).

Scheme 2

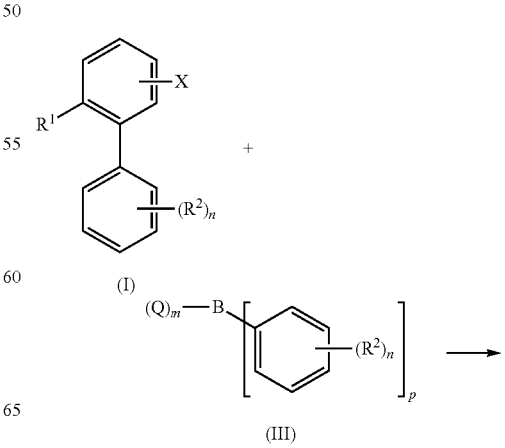

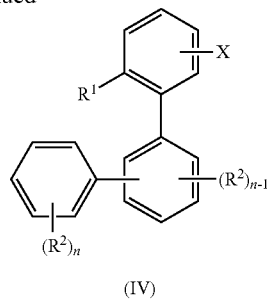

(IV)

The extent to which this further reaction takes place is essentially determined by the phosphine ligand used in the reaction.

WO 2004/052939 describes the use of biphenylic phosphines and di(tert-butyl)phenylphosphine, which catalyse the Suzuki reaction of the aryl chlorides, which are less reactive compared to aryl bromides, with phenylboronic acids even under very mild conditions. It can be assumed in such a case that triaryls are formed to a noticeable extent.

Through the introduction of a protecting group on the nitrogen atom, it is possible according to WO 2009/135598 to reduce the proportion of triaryls. In the Suzuki reaction, it is possible to use either trialkyl- or triarylphosphines.

SUMMARY

It was an object of the present invention to find a ligand which allows formation of triaryls to a very small degree, if any, and thus enables more economically viable access to chlorinated biphenylanilides or biphenylanilines The object is surprisingly achieved by an improved process for preparing chlorinated biphenylanilides and biphenylanilines of the formula (I)

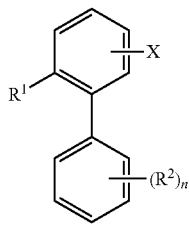

where the substituents are each defined as follows:
X is selected from hydrogen, fluorine and chlorine;
$R^1$ is selected from a protected amino group, $NO_2$, $NH_2$ and $NHR^3$;
$R^2$ is chlorine;
$R^3$ is selected from hydrogen, $-CH_2-(C=O)CH_3$, $C_1$-$C_8$-alkyl, $C_1$-$C_8$-alkenyl, $C_1$-$C_8$-alkynyl and $C_6$-$C_{18}$-aryl;
n is selected from 1, 2 and 3,
by reacting haloaromatics of the general formula (II)

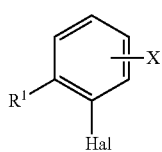

in which
Hal is selected from bromine and iodine; and X and $R^1$ are each as defined above,
in the presence of a base and a palladium catalyst selected from the group consisting of
a) a complex consisting of palladium in the 0 oxidation state and a phosphine ligand of the formula (V) or a salt thereof,
b) a palladium salt in the presence of a phosphine ligand of the formula (V) or a salt thereof and
c) metallic palladium, optionally applied to a support, in the presence of a phosphine ligand of the formula (V) or a salt thereof,
where the phosphine ligand of the formula (V) is defined as follows:

where
$R^6$ is selected from hydrogen, $C_1$-$C_4$ alkyl, $C_1$-$C_4$ haloalkyl, phenyl and $NR^7$ and
$R^7$ is selected from $(C_1$-$C_4$-alkyl$)_2$
or a salt thereof,
in a solvent, with an organoboron compound of the formula (III)

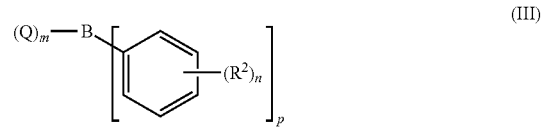

selected from the group consisting of:
(i) boronic acids of the formula (III) in which
m is 2,
p is 1,
$Q^1$ and $Q^2$ are each hydroxyl groups,
$R^2$ and n are each as defined above,
or the anhydrides, dimers or trimers formed from the boronic acids of the formula (III);
(ii) boronic acid derivatives of the formula (III) in which
m is 2,
p is 1,
$Q^1$ and $Q^2$ are each independently selected from F, Cl, Br, I, $C_{1-4}$-alkyl-, $C_{6-10}$-aryl-, $C_{1-4}$-alkoxy- and $C_{6-10}$-aryloxy,
$R^2$ and n are each as defined above;
(iii) borinic acids of the formula (III) in which
m is 1,
p is 2,
Q is selected from OH, F, Cl, Br, I, $C_{1-4}$-alkyl, $C_{6-10}$-aryl, $C_{1-4}$-alkoxy and $C_{6-10}$-aryloxy radicals,
$R^2$ and n are each as defined above;
(iv) cyclic boronic esters of the formula (III) in which
m is 2,
P is 1,
$Q^1$ and $Q^2$ are each independently selected from $C_{1-4}$-alkoxy radicals which, together with the boron atom to which they are bonded, form a 5- or 6-membered ring which may be substituted by $C_{1-4}$-alkyl radicals,
$R^2$ and n are each as defined above;

(v) boronates of the formula (III) in which
m is 3,
p is 1,
$R^2$ and n are each as defined above,
$Q^1$ to $Q^3$ are each independently selected from OH, F, Cl, Br, I, $C_{1-4}$-alkyl, $C_{6-40}$-aryl, $C_{1-4}$-alkoxy and $C_{6-10}$-aryloxy radicals,
and in which the negative charge of the boronate anion is compensated for by a cation;
(vi) triarylboranes of the formula (III) in which
m is 0,
is 3,
$R^2$ and n are each as defined above;
(vii) tetraarylborates of the formula (III) in which
m is 0,
p is 4,
$R^2$ and n are each as defined above,
and in which the negative charge of the boronate anion is compensated for by a cation.

One embodiment of the present invention relates to the above-described process for preparing substituted biphenylanilides of the formula (I)

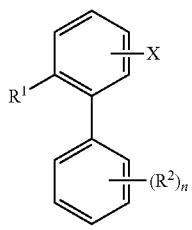

(I)

in which
X is selected from hydrogen, fluorine and chlorine;
$R^1$ is selected from —NH(CO)$R^3$, —N=CR$^4$R$^5$, NO$_2$, NH$_2$ and NHR$^3$;
$R^2$ is chlorine;
$R^3$, $R^4$, $R^5$ are each independently selected from hydrogen, —CH$_2$—(C=O)CH$_3$, $C_1$-$C_8$-alkyl, $C_1$-$C_8$-alkenyl, $C_1$-$C_8$-alkynyl and $C_6$-$C_{18}$-aryl; or
$R^4$, $R^5$, together with the carbon atom to which they are bonded, may form a 5- or 6-membered ring containing 1, 2 or 3 heteroatoms selected from N, O and S;
n is selected from 1, 2 and 3.

In one embodiment of the present invention, the phosphine ligand used is a compound of the formula (V-i)

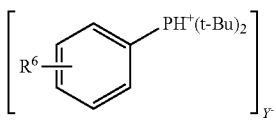

(V-i)

where
$R^6$ is selected from hydrogen, $C_1$-$C_4$ alkyl, $C_1$-$C_4$ haloalkyl, phenyl and NR$^7$ and
$R^7$ is selected from $(C_1$-$C_4$-alkyl)$_2$ and
Y is selected from the group consisting of $BF_4^-$, perchlorate and hydrogensulphate.

It has been found that, surprisingly, the use of phosphine ligands of the general formula (V)

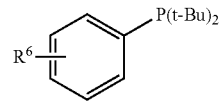

(V)

where
$R^6$ is selected from hydrogen, $C_1$-$C_4$ alkyl, $C_1$-$C_4$ haloalkyl, phenyl and NR$^7$ and
$R^7$ is selected from $(C_1$-$C_4$-alkyl)$_2$ or a salt thereof in the Suzuki reaction according to Scheme 1, gives chlorinated biphenylanilides or biphenylanilides with high selectivity and a small extent of triaryl formation.

Organoboron Compounds

The organoboron compounds which can be used in the process according to the present invention:

Boronic acids of the formula (III) in which
m is 2,
p is 1,
$Q^1$ and $Q^2$ are each hydroxyl groups,
$R^2$ and n are each as defined above,
or the anhydrides, dimers or trimers formed from the boronic acids of the formula (III),
are obtainable by conversion of arylmagnesium halides with trialkyl borates, preferably in THF as solvent. To suppress the formation of arylborinic acids, it is necessary not to use any excess of the two reagents, and to conduct the reaction at low temperatures of –60° C., as described in R. M. Washburn et al. Organic Syntheses Collective Volume 4, 68, or in Boronic Acids, editor: Dennis G. Hall, Wiley-VCH 2005, p. 28 ff., and literature references cited therein.

Examples of boronic acids which can be used according to the present invention include the following compounds:

4-chlorophenylboronic acid, 3-chlorophenylboronic acid, 2-chlorophenylboronic acid, 3,4-dichlorophenylboronic acid and 2,3-dichlorophenylboronic acid, especially 3,4-dichlorophenylboronic acid.

(ii) Boronic acid derivatives of the formula (III) in which
m is 2,
P is 1,
$Q^1$ and $Q^2$ are each independently selected from F, Cl, Br, I, $C_{1-4}$-alkyl-, $C_{6-10}$-aryl-, $C_{1-4}$-alkoxy- and $C_{6-10}$-aryloxy,
$R^2$ and n are each as defined above;
(iii) borinic acids of the formula (III) in which
m is 1,
p is 2,
Q is selected from OH, F, Cl, Br, I, $C_{1-4}$-alkyl, $C_{6-10}$-aryl, $C_{1-4}$-alkoxy and $C_{6-10}$-aryloxy radicals,
$R^2$ and n are each as defined above, are obtained by reaction of optionally substituted phenylmagnesium chloride V with trialkyl borate, preferably trimethyl borate, in tetrahydrofuran as solvent according to WO 2007/138089, as described in Scheme 3.

Scheme 3

(IV) → (V) → (III)-(iii)

Reagents: Mg/THF; 1. B(OR⁴)₃/THF, 2. acid $R^4$ is $C_1$-$C_4$-alkyl, preferably methyl.
Hal is Cl, Br, I.

Preference is given to proceeding from diphenylborinic acids of the formula (iii) in which m is 1, p is 2, Q is OH and $R^2$ and n are each as defined above.

Further starting materials are diphenylborinic acids (iii) in which n is 1 or 2, especially 2. Particular preference is given to diphenylborinic acids (iii) substituted in the 3 and 4 positions or only in the 4 position.

Borinic acids which can be used according to the present invention are selected from the group consisting of bis(3,4-dichlorophenyl)borinic acid, bis(2,3-dichlorophenyl)borinic acid, bis(3-dichlorophenyl)borinic acid, bis(4-dichlorophenyl)borinic acid, 4-chlorophenylboronic acid, 3-chlorophenylboronic acid, 2-chlorophenylboronic acid, 3,4-dichlorophenylboronic acid and 2,3-dichlorophenylboronic acid. In one embodiment of the present invention, the compound of the formula (III) is selected from bis(3,4-dichlorophenyl)borinic acid and 4-chlorophenylboronic acid.

An essential factor for a high yield of diphenylborinic acid (iii) is the use of only 0.7 eq. of trialkyl borate, based on the substituted chlorobenzene (IV) used. In the case of a use amount of 1.1 eq. of trialkyl borate, phenylboronic acid is formed, as described in EP-A 0 888 261.

The reaction temperature in this process stage is, for example, in the range from −20 to 100° C., 20 to 80° C. or 40 to 60° C.

(iv) Cyclic boronic esters of the formula (III) in which
   m is 2,
   P is 1,
   $Q^1$ and $Q^2$ are each independently selected from $C_{1-4}$-alkoxy radicals which, together with the boron atom to which they are bonded, form a 5- or 6-membered ring which may be substituted by $C_{1-4}$-alkyl radicals,
$R^2$ and n are each as defined above,
are obtainable according to Boronic Acids, editor: Dennis G. Hall, Wiley-VCH 2005, p. 28 ff. and literature references cited therein.

Examples of cyclic boronic esters which can be used according to the present invention include compounds of the following formulae (iv-1) to (iv-3):

in which $R^2$ and n are each as defined above.
(v) boronates of the formula (III) in which
   m is 3,
   p is 1,
   $R^2$ and n are each as defined above,
   $Q^1$ to $Q^3$ are each independently selected from OH, F, Cl, Br, I, $C_{1-4}$-alkyl, $C_{6-10}$-aryl, $C_{1-4}$-alkoxy and $C_{6-10}$-aryloxy radicals,
   and in which the negative charge of the boronate anion is compensated for by a cation, as shown by the formula (iv-1) below.

The cation ($M^+$) is selected, for example, from the group consisting of ammonium ($NH_4^+$), alkali metal or alkaline earth metal cations, such as $Na^+$, $K^+$, $Li^+$, $Mg^{2+}$, $Ca^{2+}$.

The boronates (v) are obtainable according to Serwatowski et al., Tetrahedron Lett. 44, 7329 (2003).

(vi) Triarylboranes of the formula (III) in which
   m is 0,
   p is 3,
   $R^2$ and n are each as defined above.

The triarylboranes (vi) are obtainable according to H. C. Brown et al., J. Organomet. Chem. 73, 1 (1988) and H. C. Brown et al., "Borane reagents", Verlag Harcourt Brace Jovanovich, (1988).

(vii) Tetraarylborates of the formula (III) in which
   m is 0,
   p is 4,
   $R^2$ and n are each as defined above,
   and in which the negative charge of the boronate anion is compensated for by a cation which is selected, for example, from the group consisting of ammonium ($NH_4^+$), alkali metal or alkaline earth metal cations, such as $Na^+$, $K^+$, $Li^+$, $Mg^{2+}$, $Ca^{2+}$.

The tetraaryl borates (vii) are obtainable according to J. Serwatowski et al., Tetrahedron Lett. 44, 7329 (2003).

Suzuki Coupling

According to the present invention, chlorinated biphenylanilides and biphenylanilines of the formula (I) can be prepared in high selectivity and with high yields.

By using phosphine ligands of the general formula (V)

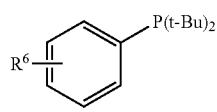

where
R⁶ is selected from hydrogen, $C_1$-$C_4$ alkyl, $C_1$-$C_4$ haloalkyl, phenyl and NR⁷ and
R⁷ is selected from $(C_1$-$C_4$-alkyl$)_2$
or a salt thereof,
it is possible to reduce the proportion of triaryls compared to the use of aliphatic phosphine ligands. R¹ in this formula (I) or (II) may be a protected amino group, $NO_2$, $NH_2$ and NHR³, where R³ is as defined above.

As disclosed in WO 2009/135598, the Suzuki coupling can be conducted under milder reaction conditions when the amino group of the aryl halide of the formula (II) is protected by a protecting group. Therefore, the formation of unwanted by-products, such as dehalogenation products, triaryls and polychlorinated biphenyls (PCBs), is considerably reduced.

"Protecting group" in this context means any kind of chemical group which can be used to modify the amino group of the aryl halide of the formula (II) during the Suzuki coupling step and, after the coupling, can be detached to reform the original amine of the substituted biphenylanilide of the formula (I), for example by reaction with aqueous acid. This step is referred to as deprotection.

Examples of protecting groups which can generally be used for the protection of amine groups include the following groups:

Schiff bases (RR"C=N—R'), which are obtained by reaction of the amino group with an aldehyde or ketone. The Schiff base protecting group can be detached, for example, by acid treatment, by hydrogenation with Pd/C/hydrogen according to J. Am. Chem. Soc. 1960, 82, 5688, or with hydrazine in ethanol according to J. Chem. Soc. C, 1969, 1758.

Preference is given to using ketones such as acetone, benzophenone or pinacolone, or aldehydes such as formaldehyde, acetaldehyde or benzaldehyde.

Acetylamino and acetoacetylamino groups are obtained by reaction of the amino group with acetic acid or with acetoacetic esters. The groups can be detached by acid treatment.

In one embodiment of the present invention, the amino group of the aryl halide of the formula (II) is protected by a Schiff base, by an acetylamino group or by an acetoacetylamino group.

In a further preferred embodiment of the invention,
X is selected from hydrogen, fluorine and chlorine;
R¹ is selected from —NH(CO)R³, —N=CR⁴R⁵ and $NH_2$;
R² is chlorine;
R³, R⁴, R⁵ are each independently selected from hydrogen, —$CH_2$—(C=O)—$C_{1-8}$-alkyl, $C_{1-8}$-alkyl, $C_{1-8}$-alkenyl, $C_{1-8}$-alkynyl and $C_{6-18}$-aryl; or
R⁴, R⁵ together with the carbon atom to which they are bonded can form a five- or six-membered ring having one, two or three heteroatoms selected from N, O and S; and
n is selected from 1, 2 and 3.

In another embodiment of the invention, the substituted biphenyls prepared by the process according to the invention have the following substituents, each either individually or in combination:

X is selected from hydrogen, fluorine and chlorine;
R¹ is selected from —NH(CO)$CH_3$ and $NH_2$;
R² is chlorine;
n is selected from 1 and 2, preferably 2.

The homogeneously catalysed Suzuki biaryl cross-coupling which follows is conducted according to Scheme 1.

Scheme 1

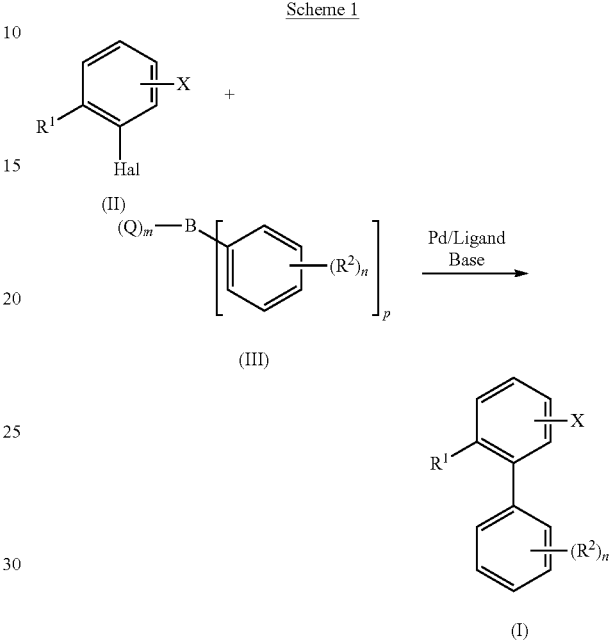

where the ligand used is a compound of the formula (V) or a salt thereof. The substituents are as described above.

The phosphine ligand of the formula (V) may also be used in the form of a phosphonium salt, for example as a tetrafluoroborate (Org. Lett. 2001, 3, 4295), perchlorate or hydrogensulphate, and can be released therefrom in situ by base.

The base used can, as well as the neutralization of the acid that forms, also have a positive effect on the course of the reaction through an activation of the arylboronic acid to give anionic boronate species. As well as the abovementioned bases, such an activation can also be achieved through addition of fluoride salts, for example CaF, NaF, KF, LiF or CsF.

The palladium catalysts used are generally produced in situ from at least one palladium(II) salt or a palladium(0) compound and the appropriate phosphine ligands. However, they can also be used directly in the form of the palladium(0) compound, without any reduction in the initial catalytic activity as a result.

The preparation examples below distinctly show the surprising advantage of the arylalkylphosphine ligand of the formula (V), for example [(t-Bu)$_2$PhPH]BF$_4$, over an alkylphosphine ligand, for example [(t-Bu)$_3$PH]BF$_4$. The inventive use of the ligand of the formula (V) or of a salt thereof leads to a distinct reduction in formation of triaryls compared to the use of alkylphosphine ligands, for example [(t-Bu)$_3$PH]BF$_4$.

Examples of the compound (II) are selected from the group consisting of N-(2-bromo-4-fluorophenyl)acetamide, N-(2-bromophenyl)acetamide, N-(2-bromophenyl)-3-oxobutanamide, N-(2-bromo-4-fluorophenyl)-3-oxobutanamide, 2-bromo-N-(propan-2-ylidene)aniline, 2-bromo-4- fluoro-N-(propan-2-ylidene)aniline, 2-bromo-4-fluoroaniline, 2-bromoaniline.

The present invention therefore also provides the above-described process wherein the compound (II) is selected from the group consisting of N-(2-bromo-4-fluorophenyl)acetamide, N-(2-bromophenyl)acetamide, N-(2-bromophenyl)-3-oxobutanamide, N-(2-bromo-4-fluorophenyl)-3-oxobutanamide, 2-bromo-N-(propan-2-ylidene)aniline, 2-bromo-4-fluoro-N-(propan-2-ylidene)aniline, 2-bromo-4-fluoroaniline, 2-bromoaniline The compound (II) is used, based on the organoboron compound (III) (boron equivalents), normally in an equimolar amount, preferably with an up to 20 percent excess, especially with an up to 50 percent excess, very specifically with an up to 100 percent excess.

Preferred compounds of the formula (III) include both borinic acids of the formula (III) (iii) and boronic acids of the formula (III) (i) or (ii). For reasons of economic viability, preference is given to the use of borinic acids of the formula (III) (iii).

Examples of preferred compounds of the formula (III) are selected from the group consisting of bis(3,4-dichlorophenyl)borinic acid, bis(2,3-dichlorophenyl)borinic acid, bis(3-dichlorophenyl)borinic acid, bis(4-dichlorophenyl)borinic acid, 4-chlorophenylboronic acid, 3-chlorophenylboronic acid, 2-chlorophenylboronic acid, 3,4-dichlorophenylboronic acid and 2,3-dichlorophenylboronic acid.

Preferred compounds of the formula (III) are also selected from the group consisting of bis(3,4-dichlorophenyl)borinic acid, bis(2,3-dichlorophenyl)borinic acid, bis(3-dichlorophenyl)borinic acid, and bis(4-dichlorophenyl)borinic acid.

Examples of combinations of compounds (II) and (III) according to the present invention are:

Compound (II) is 2-bromo-4-fluoroacetanilide and compound (III) is selected from the group consisting of bis(3,4-dichlorophenyl)borinic acid, bis(2,3-dichlorophenyl)borinic acid, bis(3-dichlorophenyl)borinic acid, bis(4-dichlorophenyl)borinic acid, 4-chlorophenylboronic acid, 3-chlorophenylboronic acid, 2-chlorophenylboronic acid, 3,4-dichlorophenylboronic acid and 2,3-dichlorophenylboronic acid.

Compound (II) is 2-bromo-4-fluoroaniline and compound (III) is selected from the group consisting of bis(3,4-dichlorophenyl)borinic acid, bis(2,3-dichlorophenyl)borinic acid, bis(3-dichlorophenyl)borinic acid, bis(4-dichlorophenyl)borinic acid, 4-chlorophenylboronic acid, 3-chlorophenylboronic acid, 2-chlorophenylboronic acid, 3,4-dichlorophenylboronic acid and 2,3-dichlorophenylboronic acid.

Compound (II) is 2-bromoacetanilide and compound (III) is selected from the group consisting of bis(3,4-dichlorophenyl)borinic acid, bis(2,3-dichlorophenyl)borinic acid, bis(3-dichlorophenyl)borinic acid, bis(4-dichlorophenyl)borinic acid, 4-chlorophenylboronic acid, 3-chlorophenylboronic acid, 2-chlorophenylboronic acid, 3,4-dichlorophenylboronic acid and 2,3-dichlorophenylboronic acid.

Compound (II) is 2-bromoaniline and compound (III) is selected from the group consisting of bis(3,4-dichlorophenyl)borinic acid, bis(2,3-dichlorophenyl)borinic acid, bis(3-dichlorophenyl)borinic acid, bis(4-dichlorophenyl)borinic acid, 4-chlorophenylboronic acid, 3-chlorophenylboronic acid, 2-chlorophenylboronic acid, 3,4-dichlorophenylboronic acid and 2,3-dichlorophenylboronic acid.

In a further embodiment of the present invention, the compound (II) is 2-bromo-4-fluoroacetanilide and the compound (III) is bis(3,4-dichlorophenyl)borinic acid.

In a further embodiment of the present invention, the compound (II) is 2-bromo-4-fluoroaniline and the compound (III) is bis(3,4-dichlorophenyl)borinic acid.

In a further embodiment of the present invention, the compound (II) is 2-bromoacetanilide and the compound (III) is 4-chlorophenylboronic acid.

In a further embodiment of the present invention, the compound (II) is 2-bromoaniline and the compound (III) is 4-chlorophenylboronic acid.

Bases used may be organic bases, for example tertiary amines Preference is given to using, for example, triethylamine or dimethylcyclohexylamine Bases used are preferably alkali metal hydroxides, alkaline earth metal hydroxides, alkali metal carbonates, alkaline earth metal carbonates, alkali metal hydrogencarbonates, alkali metal acetates, alkaline earth metal acetates, alkali metal alkoxides and alkaline earth metal alkoxides, in a mixture and especially individually. Particularly preferred bases are alkali metal hydroxides, alkaline earth metal hydroxides, alkali metal carbonate, alkaline earth metal carbonate and alkali metal hydrogencarbonates. Especially preferred bases are alkali metal hydroxides, e.g. sodium hydroxide and potassium hydroxide, and also alkali metal carbonates and alkali metal hydrogencarbonates, e.g. lithium carbonate, sodium carbonate and potassium carbonate. Accordingly, in one embodiment of the present invention, the base is selected from alkali metal hydroxides, alkali metal carbonates and alkali metal hydrogencarbonates. In a further embodiment of the present invention, the base is selected from NaOH, KOH, $Li_2CO_3$, $Na_2CO_3$ and $K_2CO_3$. The base is used in the process according to the invention preferably with a proportion of 100 to 500 mol %, further preferably 150 to 400 mol %, based on the amount of organoboron compound (III).

Suitable palladium catalysts are palladium-ligand complexes having palladium in the zero oxidation state, palladium salts in the presence of complex ligands or optionally supported metallic palladium, in the presence of phosphine ligands of the general formula (V)

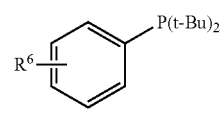

(V)

where
$R^6$ is selected from hydrogen, $C_1$-$C_4$ alkyl, $C_1$-$C_4$ haloalkyl, phenyl and $NR^7$ and
$R^7$ is selected from $(C_1$-$C_4$-alkyl$)_2$,
or a salt thereof.

In a further embodiment of the present invention,
$R^6$ is selected from hydrogen, methyl, difluoromethyl and trifluoromethyl, and
$R^7$ is $(CH_3)_2$.

In one embodiment of the present invention, the phosphine ligands of the general formula (V) are selected from di(tert-butyl)phenylphosphine, di-tert-butyl-p[4-(trifluoromethyl)phenyl]phosphine, 4-(di-tert-butylphosphino)-p-N,N-dimethylaniline and di-tert-butyl-p-(4-methylphenyl)phosphine.

In a further embodiment of the present invention, the phosphine ligand of the general formula (V) is di(tert-butyl)phenylphosphine.

The present invention also provides a compound of the formula (V)

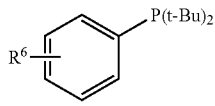

where
R[6] is selected from hydrogen, $C_1$-$C_4$ alkyl, $C_1$-$C_4$ haloalkyl, phenyl and NR[7] and
R[7] is selected from $(C_1$-$C_4$-alkyl)$_2$.

The present invention further provides a compound of the formula (V)

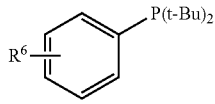

where
R[6] is selected from hydrogen, methyl, mono- to trihalogenated methyl and NR[7] and
R[7] is $(CH_3)_2$.

The phosphines shown in formula (V) can also be used in the form of salts thereof, for example in the form of the tetrafluoroborate, perchlorate or hydrogensulphate, and released in situ by addition of a base.

The present invention further provides a compound of the formula (V-i)

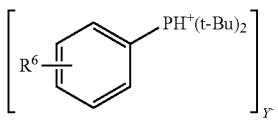

where
R[6] is selected from hydrogen, $C_1$-$C_4$ alkyl, $C_1$-$C_4$ haloalkyl, phenyl and NR[7] and
R[7] is selected from $(C_1$-$C_4$-alkyl)$_2$ and
Y is selected from the group consisting of $BF_4^-$, perchlorate and hydrogensulphate.

In one embodiment of the present invention, the palladium catalyst is selected from the group consisting of:
a) a complex consisting of palladium in the 0 oxidation state and a phosphine ligand of the formula (V) or a salt thereof,
b) a palladium salt in the presence of a phosphine ligand of the formula (V) or a salt thereof and
c) metallic palladium, optionally applied to a support, in the presence of a phosphine ligand of the formula (V) or a salt thereof.

One embodiment of the present invention is the above-described process wherein the palladium catalyst a) is a complex of palladium in the 0 oxidation state and a phosphine ligand of the formula (V) or a salt thereof.

A further embodiment of the present invention is the above-described process wherein a palladium catalyst b) is used. In a further embodiment, the salt of the palladium catalyst b) is selected from the group consisting of palladium chloride, palladium acetate, palladium acetylacetonate and bis(acetonitrile)palladium chloride.

A further embodiment of the present invention is the above-described process wherein a palladium catalyst c) is used, and this palladium catalyst c) consists of metallic palladium on activated carbon in the presence of a phosphine ligand of the general formula (V) or a salt thereof.

The reactivity of the complex ligands can be enhanced by addition of a quaternary ammonium salt such as tetra-n-butylammonium bromide (TBAB) (see, for example, D. Zim et al., Tetrahedron Lett. 2000, 41, 8199). If required, the water solubility of the palladium complexes can be improved by various substituents, such as sulpho or sulphonate groups, carboxylic acid or carboxylate groups, phosphonic acid, phosphonium or phosphonate groups, peralkylammonium, hydroxyl and polyether groups.

From the palladium ligand complexes having palladium in the zero oxidation state, preference is given to using tetrakis(triphenylphosphine)palladium and additionally tetrakis[tri(o-tolyl)phosphine]palladium. In the palladium salts which are used in the presence of complex ligands, the palladium is normally present in the double positive oxidation state. In a preferred embodiment of the present invention, the palladium catalyst b) is selected from the group consisting of palladium chloride, palladium acetate, palladium acetylacetonate and bis(acetonitrile)palladium chloride. Particular preference is given to using palladium acetylacetonate.

The molar ratio of palladium to the phosphine ligand of the formula (V) or one of the salts thereof should be between 4:1 and 1:100, and is preferably between 1:1 and 1:5, more preferably between 1:1 and 1:2.

When optionally supported metallic palladium is used, particular preference is given to the additional use of the aforementioned phosphine ligands of the formula (V) or (V-i). The palladium catalyst is used in the process according to the invention in a small proportion of 0.001 to 1.0 mol %, preferably 0.005 to 0.5 mol % or 0.01 to 0.5 mol % and especially 0.005 to 0.05 mol %, based on the amount of compound (II).

The process according to the invention can be conducted in a biphasic system composed of aqueous phase and solid phase, i.e. the catalyst. The aqueous phase may also comprise a water-soluble organic solvent as well as water.

Organic solvents suitable for the process according to the invention are ethers such as dimethoxyethane, diethylene glycol dimethyl ether, tetrahydrofuran, dioxane and tert-butyl methyl ether, hydrocarbons such as n-hexane, n-heptane, cyclohexane, benzene, toluene and xylene, alcohols such as methanol, ethanol, 1-propanol, 2-propanol, ethylene glycol, 1-butanol, 2-butanol and tert-butanol, ketones such as acetone, ethyl methyl ketone and isobutyl methyl ketone, amides such as dimethylformamide, dimethylacetamide and N-methylpyrrolidone, each individually or in a mixture.

Preferred solvents are ethers such as dimethoxyethane, tetrahydrofuran and dioxane, hydrocarbons such as cyclohexane, toluene and xylene, alcohols such as ethanol, 1-propanol, 2-propanol, 1-butanol and tert-butanol, each individually or in a mixture. In a particularly preferred variant of the process according to the invention, one or more water-insoluble and one or more water-soluble solvents are used, for example mixtures of water and dioxane or water and tetrahydrofuran or water, dioxane and ethanol or water, tetrahydrofuran and methanol or water, toluene and tetrahydrofuran, preferably water and tetrahydrofuran or water, tetrahydrofuran and methanol.

In one embodiment of the present invention, the reaction is conducted in a mixture of water and an organic solvent. In a further embodiment of the present invention, the reaction is conducted in a mixture of water and 1-butanol.

The total amount of solvent is normally 3000 to 500 g and preferably 2000 to 700 g per mole of the compound (II).

Appropriately, for performance of the process, the compound (II), the organoboron compound (III), the base and the catalytically active amount of the palladium catalyst are added to a mixture of water and one or more inert organic solvents, and stirred at a temperature of 20° C. to 100° C., preferably 50° C. to 90° C., further preferably 60° C. to 80° C., over a period of 1 to 50 hours, preferably 2 to 24 hours.

According to the solvent used and temperature used, a pressure of 1 bar to 6 bar is established, preferably 1 bar to 4 bar. Preference is given to performing the reaction in water and tetrahydrofuran. The reaction can be conducted in customary apparatuses suitable for processes of this kind. After the reaction has ended, palladium catalyst obtained in solid form is removed, for example by filtration, and the crude product is freed of the solvent or solvents. In the case of products that are not entirely water-soluble, water-soluble palladium catalysts or complex ligands are removed completely in the separation of the water phase from the crude product. Subsequently, a further purification can be effected by methods known to those skilled in the art and appropriate for the particular product, for example by recrystallization, distillation, sublimation, zone melting, melt crystallization or chromatography.

The process according to the invention can be used, for example, to prepare the following compounds:

N-(3',4'-dichloro-5-fluorobiphenyl-2-yl)acetamide, 3',4'-dichloro-5-fluorobiphenyl-2-amine, N-(4'-chlorobiphenyl-2-yl)acetamide, 4'-chlorobiphenyl-2-amine Further examples are: 3',4'-dichloro-5-fluoro-N-(propan-2-ylidene)biphenyl-2-amine, 3',4'-dichloro-N-(propan-2-ylidene)biphenyl-2-amine, 4'-chloro-N-(propan-2-ylidene)biphenyl-2-amine, N-(4'-chloro-5-fluorobiphenyl-2-yl)acetamide, N-(3',4'-dichlorobiphenyl-2-yl)acetamide.

The process according to the invention affords the compounds of the formula (I) in very high quantitative yields with very good purity. The substituted biphenyls obtainable by the process according to the invention are suitable as precursors for fungicidal crop protection active ingredients (see WO 03/070705). When an amine protecting group is used, it is detached in most cases before the further conversion of the amines

PREPARATION EXAMPLES

General Procedure for Biaryl Synthesis

Under argon, a mixture of aniline or acetanilide (1.0 equivalent), chlorinated diphenylborinic acid (0.5 equivalent) or chlorinated phenylboronic acid (1.0 equivalent), base, [(t-Bu)3PH]BF4 or [(t-Bu)2PhPH]BF4 (0.12 mol %), Pd(acac)2 (0.12 mol %) is heated to 60° C. in 8 ml of water and 2 ml of 1-butanol. The reaction mixture is stirred at 60° C. for about 20 hours, cooled to room temperature and acidified with 1 N hydrochloric acid. After extracting the reaction mixture twice with ethyl acetate, the combined organic phases are dried over magnesium sulphate. The solvent is distilled off under reduced pressure.

In accordance with the general procedure, the following biaryls were prepared:
1. N-(3',4'-dichloro-5-fluorobiphenyl-2-yl)acetamide (biaryl 1)
2. 3',4'-dichloro-5-fluorobiphenyl-2-amine (biaryl 2)
3. N-(4'-chlorobiphenyl-2-yl)acetamide (biaryl 3)
4. 4'-chlorobiphenyl-2-amine (biaryl 4)

Table 1 shows batch size and reagents.

TABLE 1

| Biaryl | Aniline/anilide | Batch size [mmol] | Boron compound | base | Equivalents of base |
|---|---|---|---|---|---|
| 1 | A-1 | 4.3 | B-1 | K₂CO₃ | 1.74 |
| 2 | A-2 | 5.7 | B-1 | K₂CO₃ | 1.74 |
| 3 | A-3 | 4.6 | B-2 | phosphate buffer pH 7-10 | 2.18 20 ml/0.5M |
| 4 | A-4 | 5.7 | B-2 | K₂CO₃ | 1.74 |

Aniline/Anilide
  A-1: 2-bromo-4-fluoroacetanilide
  A-2: 2-bromo-4-fluoroaniline
  A-3: 2-bromoacetanilide
  A-4: 2-bromoaniline
Boron Compound
  B-1: bis(3,4-dichlorophenyl)borinic acid
  B-2: (4-chlorophenyl)boronic acid Table 2 shows the proportion (area %, GC-MS) of triaryls formed in the reaction mixture when preparing the biaryls 1 to 4 as a function of the ligand used.

TABLE 2

| Biaryl | 1 | | 2 | | 3 | | 4 | |
|---|---|---|---|---|---|---|---|---|
| Ligand | A | B | A | B | A | B | A | B |
| Triaryl [area %, GC-MS] | 5.6 | 3.3 | 2.1 | 0.9 | 0.3 | 0 | 3.5 | 0.5 |

Ligand A: [(t-Bu)3PH]BF4
Ligand B: [(t-Bu)2PhPH]BF4

EXAMPLE

Preparation of N-(3',4'-dichloro-5-fluorobiphenyl-2-yl)acetamide

Under argon, a mixture of N-(2-bromo-4-fluorophenyl)acetamide (1.00 g, 4.27 mmol), bis(3,4-dichlorophenyl)borinic acid (0.685 g, 2.14 mmol), potassium carbonate (1.03 g, 7.44 mmol), [(t-Bu)₂PhPH]BF₄ (1.6 mg, 5.2 µmol), Pd(acac)₂ (1.6 mg, 5.3 µmol) was heated to 60° C. in 8 ml of water and 2 ml of 1-butanol. The reaction mixture was stirred at 60° C. for about 13 hours, cooled to room temperature and acidified with 1 N hydrochloric acid. After extracting the reaction mixture twice with ethyl acetate, the combined organic phases were dried over magnesium sulphate. The solvent was distilled off under reduced pressure. 1.21 g of crude product were obtained (90.8 area % HPLC, 86% yield).

The invention claimed is:
1. A process for preparing a halogenated biphenylanilide of formula (I)

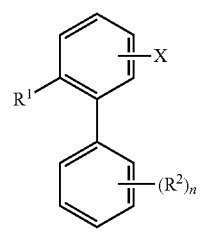

in which
X is selected from the group consisting of hydrogen, fluorine and chlorine;
$R^1$ is selected from the group consisting of —NH(CO)$R^3$, —N═C$R^4R^5$, $NO_2$, $NH_2$ and $NHR^3$;
$R^2$ is chlorine;
$R^3$, $R^4$, $R^5$ are each independently selected from the group consisting of hydrogen, —$CH_2$—(C═O)$CH_3$, $C_1$-$C_8$-alkyl, $C_1$-$C_8$-alkenyl, $C_1$-$C_8$-alkynyl and $C_6$-$C_{18}$-aryl; or
$R^4$, $R^5$, together with the carbon atom to which they are bonded, may form a 5- or 6-membered ring containing 1, 2 or 3 heteroatoms selected from N, O and S;
n is selected from 1, 2 and 3,
by reacting a compound of the formula (II)

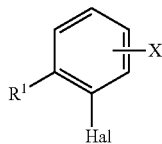
(II)

in which
Hal is selected from the group consisting of bromine and iodine; and $R^1$ and X are each as defined above, in the presence of a base and a palladium catalyst selected from the group consisting of:
a) a complex consisting of palladium in the 0 oxidation state and a phosphine ligand of the formula (V) or a salt thereof,
b) a palladium salt in the presence of a phosphine ligand of the formula (V) or a salt thereof and
c) metallic palladium, optionally applied to a support, in the presence of a phosphine ligand of the formula (V) or a salt thereof,
where the phosphine ligand of the formula (V) is defined as follows:

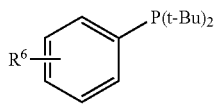
(V)

wherein
$R^6$ is selected from the group consisting of hydrogen, $C_1$-$C_4$ alkyl, $C_1$-$C_4$ haloalkyl, phenyl, and $NR^7_2$ and
$R^7$ is a $C_1$-$C_4$ alkyl,
or a salt thereof,
wherein the phosphine ligand of formula (V) is di(tert-butyl)phenylphosphine, di-tert-butyl-p-[4-(trifluoromethyl)phenyl]phosphine, 4-(di-tert-butylphosphino)-p-N,N-dimethylaniline or di-tert-butyl-p-(4-methylphenyl)phosphine, or a salt thereof,
in a solvent, with an organoboron compound of the formula (III)

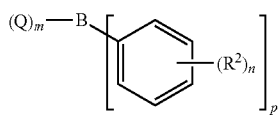
(III)

selected from the group consisting of:
(i) boronic acids of the formula (III) in which
m is 2,
p is 1,
$Q^1$ and $Q^2$ are each hydroxyl groups,
$R^2$ and n are each as defined above,
or the anhydrides, dimers or trimers formed from the boronic acids of the formula (III);
(ii) boronic acid derivatives of the formula (III) in which
m is 2,
p is 1,
$Q^1$ and $Q^2$ are each independently selected from the group consisting of F, Cl, Br, I, $C_{1-4}$-alkyl-, $C_{6-10}$-aryl-, $C_{1-4}$-alkoxy- and $C_{6-10}$-aryloxy,
$R^2$ and n are each as defined above;
(iii) borinic acids of the formula (III) in which
m is 1,
p is 2,
Q is selected from the group consisting of OH, F, Cl, Br, I, $C_{1-4}$-alkyl, $C_{6-10}$-aryl, $C_{1-4}$-alkoxy and $C_{6-10}$-aryloxy radicals,
$R^2$ and n are each as defined above;
(iv) cyclic boronic esters of the formula (III) in which
m is 2,
p is 1,
$Q^1$ and $Q^2$ are each independently a $C_{1-4}$-alkoxy radical, which,
$R^2$ and n are each as defined above;
(v) boronates of the formula (III) in which
m is 3,
p is 1,
$R^2$ and n are each as defined above,
$Q^1$ to $Q^3$ are each independently selected from the group consisting of OH, F, Cl, Br, I, $C_{1-4}$-alkyl, $C_{6-10}$-aryl, $C_{1-4}$-alkoxy and $C_{6-10}$-aryloxy radicals,
and in which the negative charge of the boronate anion is compensated for by a cation;
(vi) triarylboranes of the formula (III) in which
m is 0,
p is 3,
$R^2$ and n are each as defined above; and
(vii) tetraarylborates of the formula (III) in which
m is 0,
p is 4,
$R^2$ and n are each as defined above,
and in which the negative charge of the boronate anion is compensated for by a cation.

2. The process according to claim 1, wherein the compound (II) is selected from the group consisting of N-(2-bromo-4-fluorophenyl)acetamide, N-(2-bromophenyl)acetamide, N-(2-bromophenyl)-3-oxobutanamide, N-(2-bromo-4-fluorophenyl)-3-oxobutanamide, 2-bromo-N-(propan-2-ylidene)aniline, 2-bromo-4-fluoro-N-(propan-2-ylidene)aniline, 2-bromo-4-fluoroaniline, and 2-bromoaniline.

3. The process according to claim 1, wherein the compound of the formula (III) is selected from the group consisting of bis(3,4-dichlorophenyl)borinic acid, bis(2,3-dichlorophenyl)borinic acid, bis(3-chlorophenyl)borinic acid, bis(4-chlorophenyl)borinic acid, 4-chlorophenylboronic acid, 3-chlorophenylboronic acid, 2-chlorophenylboronic acid, 3,4-dichlorophenylboronic acid and 2,3-dichlorophenylboronic acid.

4. The process according to claim 1 wherein the base is selected from the group consisting of alkali metal hydroxides, alkali metal carbonates and alkali metal hydrogencarbonates.

5. The process according to claim 1, wherein the palladium catalyst used is palladium catalyst a).

6. The process according to claim 1, wherein a palladium catalyst b) is used.

7. The process according to claim 1, wherein a palladium catalyst c) is used, and this palladium catalyst c) comprises or consists of metallic palladium on activated carbon in the presence of a phosphine ligand of formula (V) or a salt thereof.

8. The process according to claim 6, wherein the salt of the palladium catalyst b) is used and is selected from the group consisting of palladium chloride, palladium acetate, palladium acetylacetonate and bis(acetonitrile)palladium chloride.

9. The process according to claim 1, wherein a palladium catalyst b) is used, where the molar ratio of the palladium salt to the phosphine ligand of formula (V) or a salt thereof is 1:1 to 1:5.

10. The process according to claim 1, wherein 0.001 to 1.0 mol % of the palladium catalyst is used, based on the amount of the compound of the formula (II).

11. The process according to claim 1, wherein the reaction is conducted at a temperature of 20° C. to 100° C.

12. The process according to any claim 1, wherein the reaction is conducted in a mixture of water and an organic solvent.

13. The process according to claim 1, wherein the organoboron compound is (i).

14. The process according to claim 1, wherein the organoboron compound is (ii).

15. The process according to claim 1, wherein the organoboron compound is (iii).

16. The process according to claim 1, wherein the organoboron compound is (iv).

17. The process according to claim 1, wherein the organoboron compound is (v).

18. The process according to claim 1, wherein the organoboron compound is (vi).

19. The process according to claim 1, wherein the organoboron compound is (vii).

\* \* \* \* \*